United States Patent
Andersen et al.

(10) Patent No.: US 8,771,261 B2
(45) Date of Patent: Jul. 8, 2014

(54) DYNAMIC OPTICAL SURGICAL SYSTEM UTILIZING A FIXED RELATIONSHIP BETWEEN TARGET TISSUE VISUALIZATION AND BEAM DELIVERY

(75) Inventors: Dan Andersen, Menlo Park, CA (US); David G. Angeley, Charlottesville, VA (US)

(73) Assignee: Topcon Medical Laser Systems, Inc., Santa Clara, CA (US)

( * ) Notice: Subject to any disclaimer, the term of this patent is extended or adjusted under 35 U.S.C. 154(b) by 2103 days.

(21) Appl. No.: 11/789,964

(22) Filed: Apr. 25, 2007

(65) Prior Publication Data

US 2008/0033406 A1   Feb. 7, 2008

Related U.S. Application Data

(60) Provisional application No. 60/795,918, filed on Apr. 28, 2006.

(51) Int. Cl.
*A61B 18/18* (2006.01)

(52) U.S. Cl.
USPC .................................. 606/4; 606/10; 351/211

(58) Field of Classification Search
USPC .............. 606/4–6, 10–12, 16–18; 607/88, 89; 351/205–212
See application file for complete search history.

(56) References Cited

U.S. PATENT DOCUMENTS

| | | |
|---|---|---|
| 3,703,176 A | 11/1972 | Vassiliadis et al. |
| 4,685,784 A | 8/1987 | Kirchhuebel |
| 4,884,884 A | 12/1989 | Reis |
| 4,917,486 A | 4/1990 | Raven et al. |
| 5,391,165 A | 2/1995 | Fountain et al. |
| 5,425,729 A | 6/1995 | Ishida et al. |
| 5,480,396 A | 1/1996 | Simon et al. |
| 5,488,443 A | 1/1996 | Ota et al. |
| 5,543,866 A | 8/1996 | Van De Velde |
| 5,568,208 A | 10/1996 | Van De Velde |

(Continued)

FOREIGN PATENT DOCUMENTS

| | | |
|---|---|---|
| GB | 2 252 249 A | 8/1992 |
| WO | WO 99/44491 A1 | 9/1999 |
| WO | WO 01/87181 A2 | 11/2001 |
| WO | WO 2005/065116 A2 | 7/2005 |

OTHER PUBLICATIONS

Naess et al., "Computer-Assisted Laser Photocoagulation of the Retina-A Hybrid Tracking Approach", *Journal of Biomedical Optics*, Apr. 2002, vol. 7, No. 2, pp. 179-189.

(Continued)

*Primary Examiner* — Ahmed Farah
(74) *Attorney, Agent, or Firm* — Morrison & Foerster LLP

(57) ABSTRACT

A system and method of treating target tissue that includes generating a treatment beam of light using a light source, directing the treatment beam onto target tissue using an optical element, generating an image of the target tissue from light emanating from the target tissue using a plurality of optical elements, and translating the light source, the optical element and/or the plurality of optical elements relative to the target tissue (using a translation device) to simultaneously move the treatment beam along the target tissue and the field of view of the target tissue as defined by the plurality of optical elements. Control electronics control the translation device to cause the treatment beam to move along the target tissue in a predetermined pattern.

48 Claims, 10 Drawing Sheets

(56) References Cited

U.S. PATENT DOCUMENTS

| | | | |
|---|---|---|---|
| 5,743,902 | A | 4/1998 | Trost |
| 5,777,719 | A * | 7/1998 | Williams et al. ............... 351/212 |
| 5,892,569 | A | 4/1999 | Van de Velde |
| 5,921,981 | A | 7/1999 | Bahmanyar et al. |
| 5,943,117 | A | 8/1999 | Van de Velde |
| 5,957,915 | A | 9/1999 | Trost |
| 5,971,978 | A | 10/1999 | Mukai |
| 5,980,513 | A | 11/1999 | Frey et al. |
| 6,066,128 | A | 5/2000 | Bahmanyar et al. |
| 6,096,028 | A | 8/2000 | Bahmanyar et al. |
| 6,099,522 | A | 8/2000 | Knopp et al. |
| 6,149,644 | A | 11/2000 | Xie |
| 6,186,628 | B1 | 2/2001 | Van de Velde |
| 6,267,756 | B1 | 7/2001 | Feuerstein et al. |
| 6,328,733 | B1 | 12/2001 | Trost |
| 6,347,244 | B1 | 2/2002 | Dubnack |
| 6,494,878 | B1 | 12/2002 | Pawlowski et al. |
| 6,585,723 | B1 * | 7/2003 | Sumiya ............................. 606/5 |
| 6,712,808 | B2 | 3/2004 | Fujieda |
| 6,789,900 | B2 | 9/2004 | Van de Velde |
| 7,112,194 | B2 | 9/2006 | Fujieda |
| 7,146,983 | B1 | 12/2006 | Hohla et al. |
| 2005/0197655 | A1 * | 9/2005 | Telfair et al. ....................... 606/5 |
| 2006/0100677 | A1 | 5/2006 | Blumenkranz et al. |
| 2007/0121069 | A1 * | 5/2007 | Andersen et al. ............. 351/221 |
| 2007/0126985 | A1 * | 6/2007 | Wiltberger et al. ........... 351/221 |
| 2007/0129775 | A1 * | 6/2007 | Mordaunt et al. ............... 607/88 |
| 2008/0231804 | A1 * | 9/2008 | Gagne et al. .................. 351/208 |

OTHER PUBLICATIONS

Markow et al., "An Automated Laser System for Eye Surgery", *IEEE Engineering in Medicine and Biology Magazine*, Dec. 1989, pp. 24-29.

Wright et al., "Hybrid Approach to Retinal Tracking and Laser Aiming for Photocoagulation", *Journal of Biomedical Optics*, Apr. 1997, vol. 2 No. 2, pp. 195-203.

Barrett et al., "Computer-Aided Retinal Photocoagulation System", *Journal of Biomedical Optics*, Jan. 1996, vol. 1 No. 1, pp. 83-91.

Van de Velde, "Role of the Scanning Laser Ophthalmoscope in Photodynamic Therapy of Macular Disease", *Ophthalmic Technologies X, Proceedings of SPIE*, vol. 3908 (2000)pp. 190-201.

Barrett et al., "Digital Imaging-Based Retinal Photocoagulation System", *SPIE*, vol. 2971 pp. 118-128.

Wright et al., "Initial In Vivo Results of a Hybrid Retinal Photocoagulation System", *Journal of Biomedical Optics*, Jan. 2000, vol. 5 No. 1, pp. 56-61.

International Search Report and Written Opinion received for PCT Patent Application No. PCT/US2007/010045, mailed on Mar. 25, 2008, 4 pages.

International Preliminary Report on Patentability received for PCT Patent Application No. PCT/US2007/010045, issued on Oct. 28, 2008, 4 pages.

Extended European Search Report received for European Patent Application No. 07776190.6, mailed on Apr. 1, 2010, 5 pages.

Office Action received for Japanese Patent Application No. 2009-507781, mailed on Jul. 19, 2011, 8 pages (4 pages of English Translation and 4 pages of Office Action).

* cited by examiner

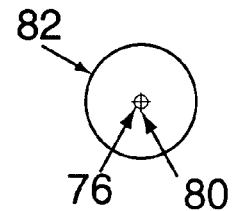
FIGURE 6
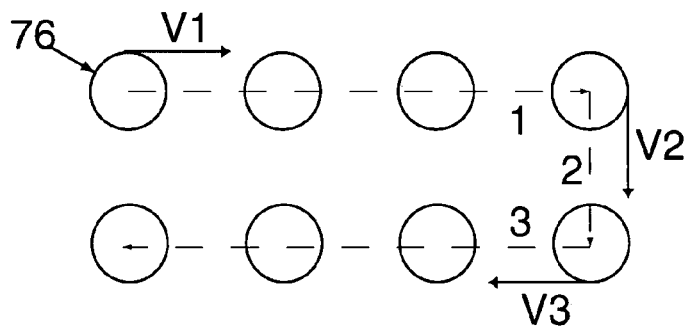
FIGURE 5
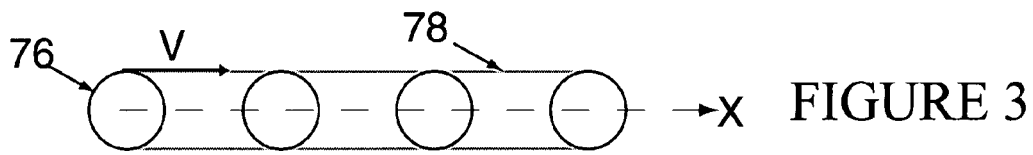
FIGURE 3
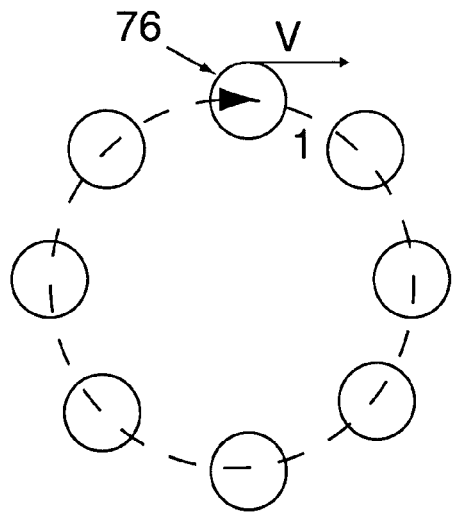
FIGURE 15
FIGURE 4
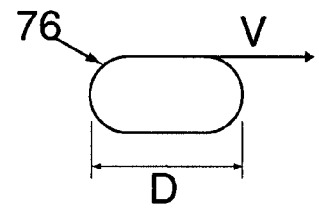

DYNAMIC OPTICAL SURGICAL SYSTEM UTILIZING A FIXED RELATIONSHIP BETWEEN TARGET TISSUE VISUALIZATION AND BEAM DELIVERY

This application claims the benefit of U.S. Provisional Application No. 60/795,918, filed Apr. 28, 2006, the contents of which are incorporated herein by reference.

FIELD OF THE INVENTION

The present invention relates to optical surgical devices and techniques, and more particularly to optical ophthalmic surgical devices for treating tissue that utilizes coupled and moving visualization and beam delivery systems.

BACKGROUND OF THE INVENTION

Photocoagulation procedures for treating retinal tears, diabetic retinopathy and other retinal disorders are well known in the art. A well known slit lamp microscope configuration has been used to provide the visualization and base for such procedures.

Traditional ophthalmic surgical laser systems include a laser source that connects to a slit lamp-mounted delivery device via an optical fiber. The treatment often times is implemented using a visible aiming beam that individually marks the location at which the laser spot will impinge the target tissue. There are usually about 1500 laser pulses delivered in a standard pan retinal photocoagulation procedure, often totaling over 90 minutes of treatment across multiple sessions. Each of these laser pulses is activated by a depression of footswitch, and the parameters of the delivered laser pulse are controlled by a control panel. This single-shot "step and repeat" approach is time consuming, fatiguing, tedious, and uncomfortable for both the physician and patient.

Other attempts to improve the safety and speed of laser surgery have been proposed. These approaches require that the underlying laser system be inordinately complicated. For example, the simultaneous multiple spot delivery devices described in U.S. Pat. Nos. 5,921,981, 6,066,128 and 6,096,028 must employ a laser system capable of producing output powers considerably greater than those of a single spot system. This increase in laser power introduces additional and considerable expense, and raises possible safety concerns.

Similarly, in order to increase the speed of the manual procedure, the approach described in Intl. Pub. No. WO 2005/065116 A2 utilizes a single beam that is scanned using scanning optics to create a pattern of sequential therapeutic laser spots first represented by an aiming beam. The scanning of a single spot in the arrangement of a pattern allows the use of a lower power laser beam and source. In order to assure that the size and shape of the patterns of spots produced by both the aiming and therapeutic beams are identical, this device employs elaborate pattern sensing and associated feedback systems. While providing a means for improving laser surgery, it also increases the system cost and complexity. Moreover, there is no deliberate correlation between the physician's visual field of view through the microscope and the patterns of spots produced by the system.

Accordingly, there is a need for a safe, cost effective, adaptable and time-efficient approach to laser surgery that produces a pattern of treatment light that is reliably generated and that is closely linked to the physician's field of view.

SUMMARY OF THE INVENTION

The present invention solves the aforementioned problems by providing a surgical device and method for translating an optical beam on target tissue in a predetermined pattern, while simultaneously moving the physician's field of view of the target tissue.

The surgical device for treating target tissue includes a light source for generating a treatment beam of light, an optical element for directing the treatment beam onto target tissue, a plurality of optical elements for generating an image of the target tissue from light emanating from the target tissue, a translation device for translating at least one of the light source, the optical element and the plurality of optical elements relative to the target tissue to simultaneously move the treatment beam along the target tissue and a field of view of the target tissue defined by the plurality of optical elements, and control electronics for controlling the translation device to cause the treatment beam to move along the target tissue in a predetermined pattern.

In an additional aspect, the surgical device for treating target tissue includes a light source for generating a treatment beam of light, a plurality of optical elements for generating an image of the target tissue from light emanating from the target tissue, a translation device for translating the light source and the plurality of optical elements relative to the target tissue to simultaneously move the treatment beam along the target tissue and a field of view of the target tissue defined by the plurality of optical elements, and control electronics for controlling the translation device to cause the treatment beam to move along the target tissue in a predetermined pattern.

The method of treating target tissue includes generating a treatment beam of light using a light source, directing the treatment beam onto target tissue using an optical element, generating an image of the target tissue from light emanating from the target tissue using a plurality of optical elements, and translating at least one of the light source, the optical element and the plurality of optical elements relative to the target tissue to simultaneously move the treatment beam along the target tissue and a field of view of the target tissue defined by the plurality of optical elements, and to cause the treatment beam to move along the target tissue in a predetermined pattern.

In another aspect, the method for treating target tissue includes generating a treatment beam of light using a light source, generating an image of the target tissue from light emanating from the target tissue using a plurality of optical elements, and translating the light source and the plurality of optical elements relative to the target tissue to simultaneously move the treatment beam along the target tissue and a field of view of the target tissue defined by the plurality of optical elements, and to cause the treatment beam to move along the target tissue in a predetermined pattern.

Other objects and features of the present invention will become apparent by a review of the specification, claims and appended figures.

BRIEF DESCRIPTION OF THE DRAWINGS

FIG. 1 is a schematic view the ophthalmic surgical device in which the laser system and microscope are translated to simultaneously move the treatment beam and the physician's field of view.

FIG. 2 is a schematic view the ophthalmic surgical device in which the microscope is translated to simultaneously move the treatment beam and the physician's field of view.

FIG. 3 is a target plane plan view of a pattern of spots of treatment light generated by the ophthalmic surgical device.

FIG. 4 is a target plane plan view of a line pattern of treatment light generated by the ophthalmic surgical device.

FIG. 5 is a target plane plan view of a two dimensional pattern of spots of treatment light generated by the ophthalmic surgical device.

FIG. 6 illustrates a target generated by the microscope indicating the location of the treatment beam on the target tissue image.

FIG. 15 is a target plane plan view of a circular pattern of spots of treatment light generated by the ophthalmic surgical device.

DETAILED DESCRIPTION OF THE PREFERRED EMBODIMENTS

The present invention is an ophthalmic surgical device and method that increases the speed and improves the safety of laser surgeries, such as retinal photocoagulation, by simultaneously moving the treatment beam and the physicians field of view (target tissue visualization).

Figure 1:
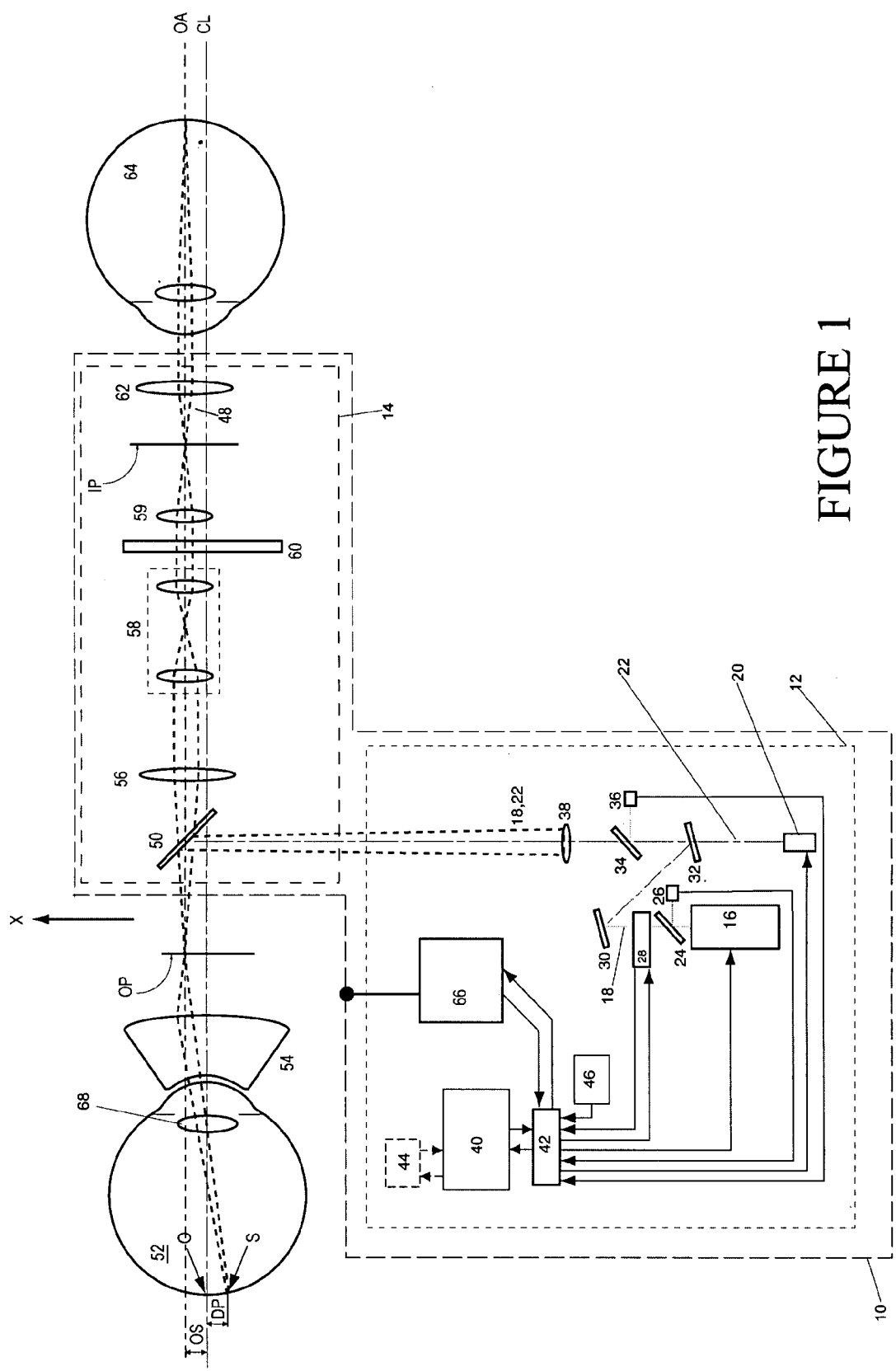

FIG. 1 illustrates the ophthalmic surgical device 10, which includes a light source assembly 12 mounted rigidly to a microscope 14. Light source assembly 12 contains a treatment light source 16 (e.g. 532 nm solid state laser, although could instead be another type of suitable light source such as gas or solid state laser, laser diode, flash lamp, light emitting diode(s), etc.) for generating a treatment beam of light 18, and an aiming light source 20 (e.g. 635 nm laser diode, although could instead be another type of suitable light source such as gas or solid state laser, laser diode, flash lamp, light emitting diode(s), etc.) for generating an aiming beam of light 22. Aiming beam 22 can be visible to the eye, or invisible if an alternate visualization scheme, such as infrared imaging, is employed. Treatment beam 18 from light source 16 first encounters mirror 24 which serves to reflect a fixed portion of the treatment light towards a photodiode for measuring the power of treatment beam 18 (for safety reasons). Treatment beam 18 then encounters a shutter 28 for controlling the delivery of the treatment beam 18 by selectively blocking the light. Treatment beam 18 then encounters a turning mirror 30 that reflects the light to mirror 32, which serves to combine treatment beam 18 and aiming beam 22 onto the same optical path. A mirror 34 and a photodiode 36 serves to sample a portion of beams 18, 22 to measure power (and to act as a redundant monitor of the state of the shutter 28). A lens 38 (e.g. a single lens, a compound lens, etc.) can be used to condition the light leaving light source assembly 12. Control electronics 40 control the light sources 16, 20 and shutter 28 via an input/output device 42. Control electronics 40 can also receive monitoring signals from shutter 28 and photodiodes 26, 36. A graphical user interface 44 and a user input device 46 (e.g. a joystick) can be used by the physician to monitor and control the system via the control electronics 40.

Microscope 14 includes a delivery mirror 50, which directs the beams 18, 22 to the patient's eye 52 via an ophthalmic lens 54. In the configuration of FIG. 1, the ophthalmic lens 54 creates a mid-air real image of the patient's retina at location OP. Delivery mirror 50 may be adjustable (movable) to selectively change the target tissue within the patient's eye 50 to which beams 18, 22 are directed. An image of the patient's eye is visualized by passing image light (visualization beam 48) from the target tissue in the patient's eye 52 through mirror 50, through an objective lens 56, through a magnification stage 58, through an eye safety filter 60, through an eyepiece lens 62, and into the physician's eye 64. The source for the imaging light is provided by an auxiliary means not shown. For example, this illumination may be provided conventionally as found on a slit lamp microscope. Eye safety filter 60 prevents therapeutic light from beam 18 from entering the physician's eye 64. Magnification stage 58 includes one or more movable optical elements (e.g. lenses) that change the magnification of the image entering the eyepiece lens 62. The magnification stage as shown may consist of the tube lens as conventionally found in the slit lamp microscope. Eyepiece lens 62 could be a plurality of optical elements that deliver the target tissue image to both eyes of the physician in the same manner as is done in well known slit lamp microscopes. The optical system in microscope 14 produces an intermediate image plane IP that is conjugate to the system object plane OP. Preferably the beams 18, 22 and 48 travel along the central optical axis OA of the microscope 14, such that the system will provide the most peripheral viewing in all directions around the target tissue as the system operates. Alternately, the microscope need not utilize a common main objective lens as shown, but may of the Greenough type. Greenough microscopes include two separate compound microscopes—one for each eye—each arranged with a different convergence angle. They are low-cost but not as flexible as other designs.

One key feature of the system is that the optical axis OA of the microscope 14 (including delivery mirror 50) is translated in a predetermined pattern relative to the patient's eye to move the beams 18, 22 on the target tissue but without deviating the visualization beam 48 away from the optical axis OA as it passes through the microscope 14. This allows for the movement of the beams 18, 22 in a pattern on the target tissue simultaneously with a corresponding change of the physician's field of view so that the peripheral viewing by the physician is not compromised (i.e. target tissue receiving the beams 18, 22 stays centered in the field of view at eyepiece lens 62). Translation is accomplished with a translation device 66 that translates the ophthalmic surgical device 10 (the light source assembly 12 and microscope 14) relative to the patient's eye 52 in a predetermined pattern. More specifically, the translation device moves the surgical device 10 relative to a head rest or other apparatus that secures the position of the patient's head. Suitable translation devices can include, but are not limited to, a motor, a piezoelectric element, a galvo, and/or a combination of these, under the control of control electronics 40.

FIG. 1 illustrates the translation of microscope 14 by an offset amount OS away from the centerline CL of the patient's eye (and/or the centerline of ophthalmic lens 54), in the direction of arrow X. This translation causes the beams 18, 22 to translate by that same amount (OS) at the point they enter lens 54, thus causing the spot at which the beams 18, 22 strike the retinal tissue of the patient's eye 52 to move from point O to point S. The actual distance between points O and S in the patient's eye 52 (based on a microscope translation distance OS) will depend upon the magnification of the optical system between location OP and the target tissue. If the mid-air image of patient's eye is magnified by a factor M, then the distance between points O and S at the target tissue (representing the displacement distance DP of beams 18, 20 at the target tissue caused by the translation of OS) will be DP=OS/M. In this particular illustration, M (which is dictated by ophthalmic lens 54 and the patient's eye optical power 68) is such that DP is less than OS.

Figure 2:
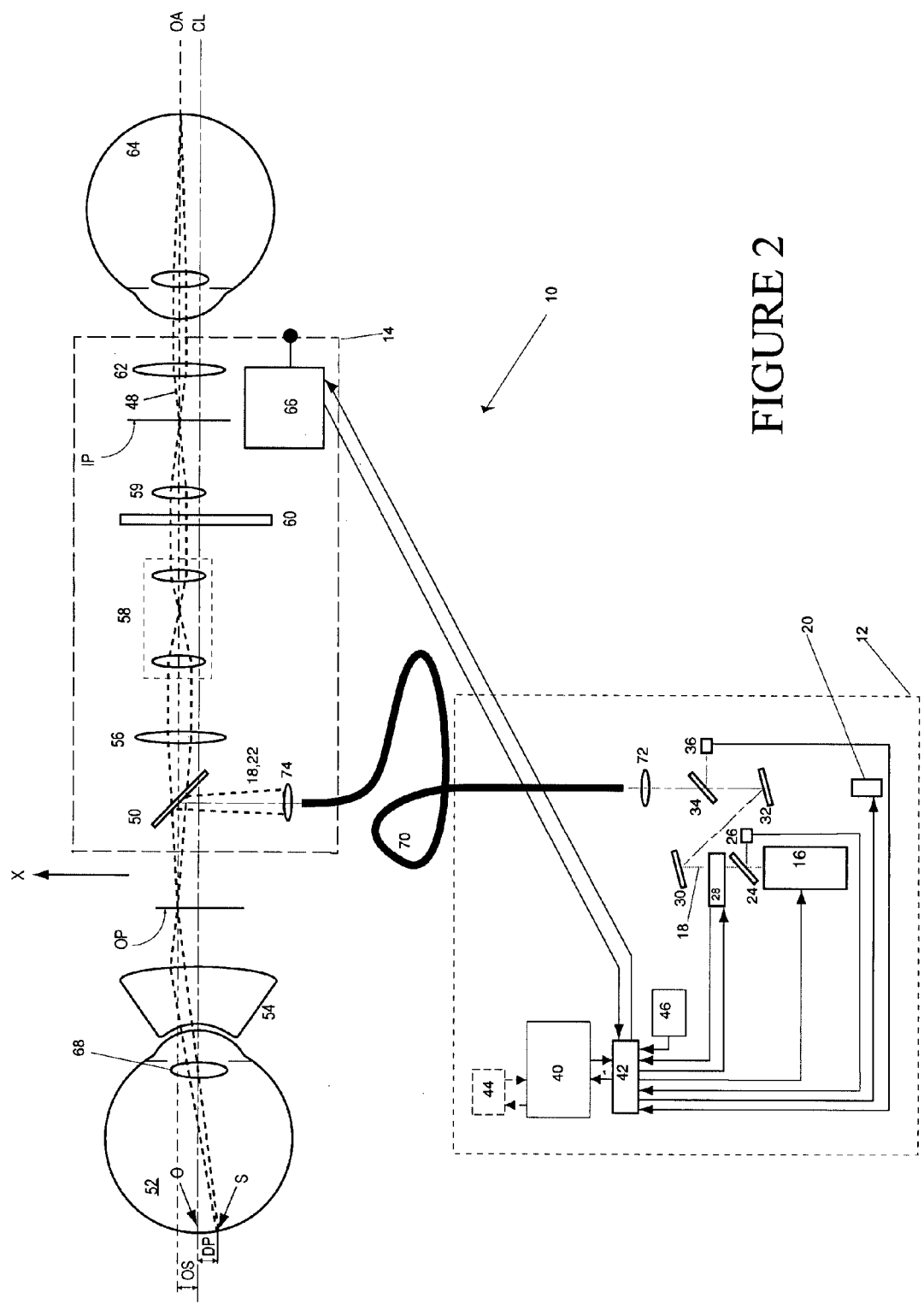

In the configuration of FIG. 1, translation device 66 moves both light source assembly 12 and microscope 14 together, which contemplates that both are integrally packaged together. FIG. 2 illustrates an alternate embodiment, where light source assembly 12 and microscope 14 are separate components, and translation device 66 only translates microscope 14 (and not light source assembly 12). In this configuration, an optical fiber 70 and lenses 72, 74 are used to deliver the beams 18, 22 to delivery mirror 50 such that relative movement between light source assembly 12 and microscope 14 do not alter the alignment of beams 18, 22 onto delivery mirror 50. In this manner, the heavier and bulkier components of light source assembly 12 need not move along with the translational movement of microscope 14 to implement the desired movement of beams 18, 22 on the target tissue.

FIGS. 1 and 2 show visualization of the patient's eye 52 via the microscope 14 by directing the image beam 48 onto the retina of the physician's eye 64. It should be noted, however, that a camera or other suitable imaging device (e.g. scanning laser ophthalmoscope, optical coherence tomography, etc.) can be used to capture the image light and reproduce the image formed thereby for the physician. The image can be displayed on an electronic display or the system graphic user interface 44.

By moving the microscope 14 (and optionally the light source assembly 12) in a predetermined pattern, it allows the physician to rapidly treat a relatively large area of target tissue in a semi-automated manner, while maintaining the beams 18, 22 at or near the center of the physician's field of vision. For example, FIG. 3 illustrates a pattern of spots 76 of the treatment beam 18 delivered to a treatment area 78 on the target tissue by moving the microscope 14 as described above. Here, the light source 16 and/or shutter 28 are configured to produce a pulsed treatment beam 18, where the microscope 14 is moved between the delivery of pulsed light. The system steps through the motion in the X direction (with velocity V) and then stops for each pulse of light, thus providing for each spot 76 to be delivered while the system is stationary. The motion is then repeated, where multiple spots 76 are delivered to the treatment area 78 by this step, stop, treat and repeat sequence. This process can be first performed using the aiming beam 22, showing the physician where the treatment beam pattern will be directed. Once the pattern of aiming spots is visually aligned to the desired treatment area 78, the physician can trigger the system to deliver the pattern of treatment light to that same treatment area 78.

While the spots 76 are shown as round, they need not necessarily be round. The pattern of light projected onto the treatment area need not be discrete spots either. The system can move the treatment beam 18 along the target tissue during a single pulse or using a continuous light source. FIG. 4 illustrates a spot 76 of treatment light moved across the treatment area while the treatment light source 16 is on and shutter 28 is open, which results is a pattern of light that constitutes a line of the treatment light on the treatment tissue. In this example, if the spot 76 has a diameter d and is moved along the target tissue at a rate of d/t in the positive x-direction, the spot provides an effective pulse duration t covering a distance D. If the treatment light source is on continuously, and thus t can be as long as possible, then a relatively long treatment area 78 can be covered by a single application of treatment beam 18. Alternately, the beam may be gated on and off, which would provide an array of spots.

The pattern of spots or lines need not be limited to just single straight lines. FIG. 5 illustrates a 2-dimensional pattern created by translating the microscope 14 in multiple directions. In this example, the system is first translated at velocity V1 to complete path 1. The system then executes a perpendicular motion along path 2 at velocity V2. Finally, the system executes another perpendicular motion along path 3 at velocity V3, completing two rows of discrete treatment spots 76. Curved paths are also possible, including arcs, circles, and random paths. The treatment light can be delivered as discrete stationary spots as shown in FIG. 5, or one or more lines (curved or straight) on the target tissue.

It should be noted that the inclusion of aiming beam source 20 and the use of aiming beam 22 is optional. If aiming beam 22 is used, the pattern of the aiming light can either replicate precisely the pattern of the treatment light (i.e. spatially superimposed on each other at the target tissue), or it can be a different pattern that indicates where the treatment light pattern will be applied. For example, the pattern for the aiming beam 18 could be a square or circle that surrounds or otherwise circumscribes the tissue that will receive the pattern of treatment beam 18.

FIG. 6 shows an alternative to the use of aiming beam 22. Instead of projecting aiming light onto the target tissue and visualizing that aiming light, a target 80 formed as indicia (i.e. a static reticle) on or between one of the optical elements used to visualize the target tissue can be used to indicate the location of the treatment pattern. This alignment scheme makes use of the fact of the fixed relationship between the visualization image 82 of the target tissue (as seen through microscope 14) and the location of spot 76 in the treatment pattern. Here target 80 is used to inform the physician of the location of the treatment beam on the target tissue. Because the imaging system of microscope 14 is moving along with the treatment beam 18 relative to the target tissue, the location of spot 76 in the image 82 does not change. Image 82 effectively serves as an alignment aid for locating the spot 76 with respect to the tissue.

Figure 7:
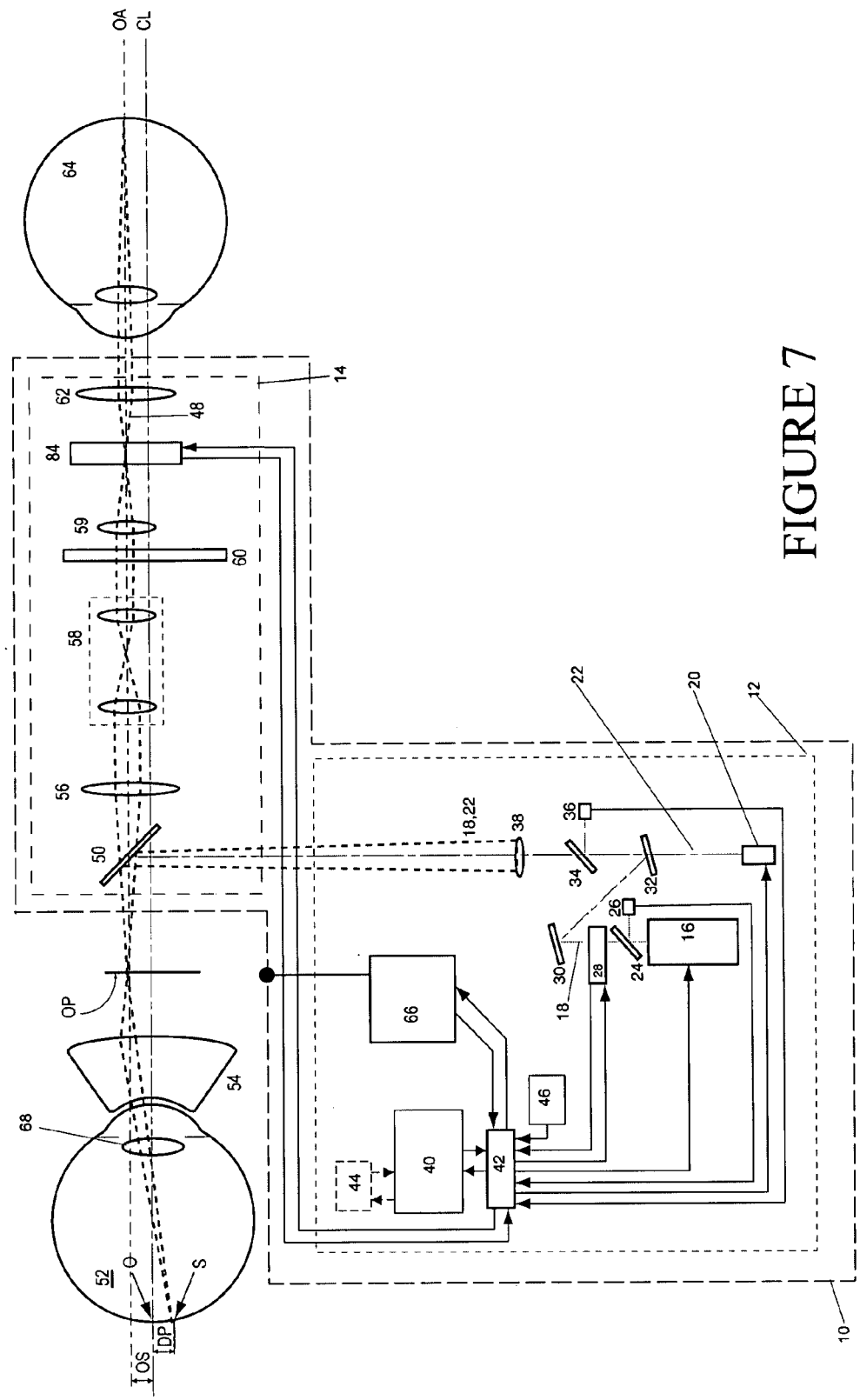
FIG. 7 is a schematic view the ophthalmic surgical device of FIG. 1 further including a reticle device indicating the location of the treatment beam on the target tissue image.
Figure 8:
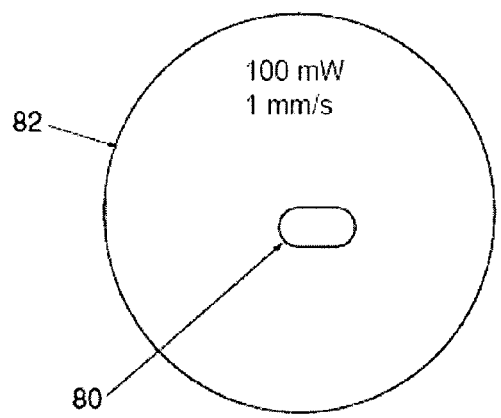
FIG. 8 illustrates the view provided by the reticle device, including system information.

FIG. 7 illustrates a configuration to implement target 80, by including a reticle device 84 at the intermediate image plane IP that generates or forms target 80. The reticle device 84 can be a passive optical element with indicia markings, or an active optical element such as an LCD or projection device that generates target 80 under the control of control electronics 40. The target 80 of reticle device 84 is aligned such that the treatment beam 18 will only be delivered to locations of the target tissue within the boundary defined by the target 80 as overlaid over the image of the target tissue. Here, the target 80 is imaged directly into the physician's eye so that it is seen as overlaid on the image of the patient's retina. In the case of an active optical reticle device, the target 80 is adjustable, to readily adapt to different system magnifications, spot sizes, treatment areas and shapes, while still providing inherent accuracy. System information, such as the laser power, pulse duration, treatment area, spot size, etc., can also be displayed to the physician by the reticle device 84, which would allow the physician access to such information dynamically without having to look away from the patient image (see FIG. 8). If the image is captured and displayed on a screen or GUI 44, only that portion of target shown within the confines of the expected treatment area to be subjected to treatment by the laser light may be shown.

Figure 9:
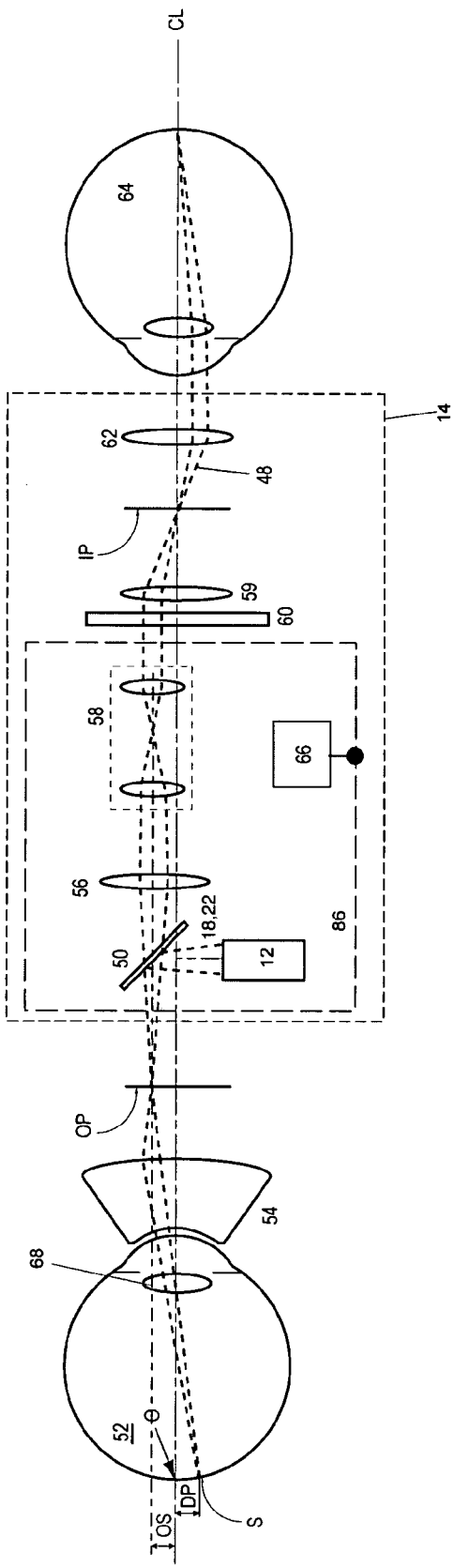
FIG. 9 is a schematic view the ophthalmic surgical device in which the laser system and a portion of the microscope are translated to simultaneously move the treatment beam and the physician's field of view.
Figure 10:
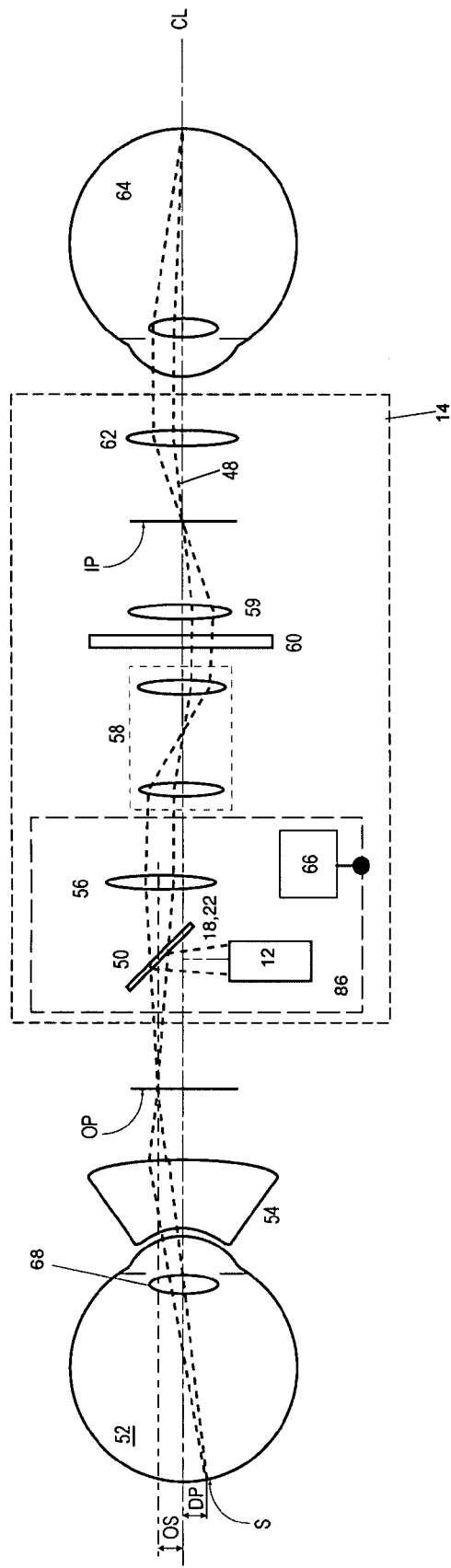
FIG. 10 is a schematic view the ophthalmic surgical device in which the laser system and a portion of the microscope are translated to simultaneously move the treatment beam and the physician's field of view.

FIG. 9 illustrates an alternate embodiment which is similar to that of FIG. 1. In this embodiment, not only is the entire light source assembly 12 contained with the microscope 14, but only a portion 86 of microscope 14 is translated to generate the pattern of treatment light on the patient's eye. Specifically, translation device 66 moves light source assembly 12, delivery mirror 50, lens 56 and magnification stage 58. The rest of the microscope components remain aligned to the centerline CL of the patient's eye. The advantage of this configuration is that only some, but not all, of the microscope components are moved by translation device 66. FIG. 10 illustrates the same embodiment, but where the magnification stage 58 is included as part of the optical elements that remain stationary instead of moving. To further eliminate the number of components being moved by translation device 66, the objective lens 56 can be located on the target tissue side of delivery mirror 50, where only the objective lens 56 is translated by translation device 66 to move the beams 18, 22 over the target tissue (as shown in FIG. 11).

Figure 11:
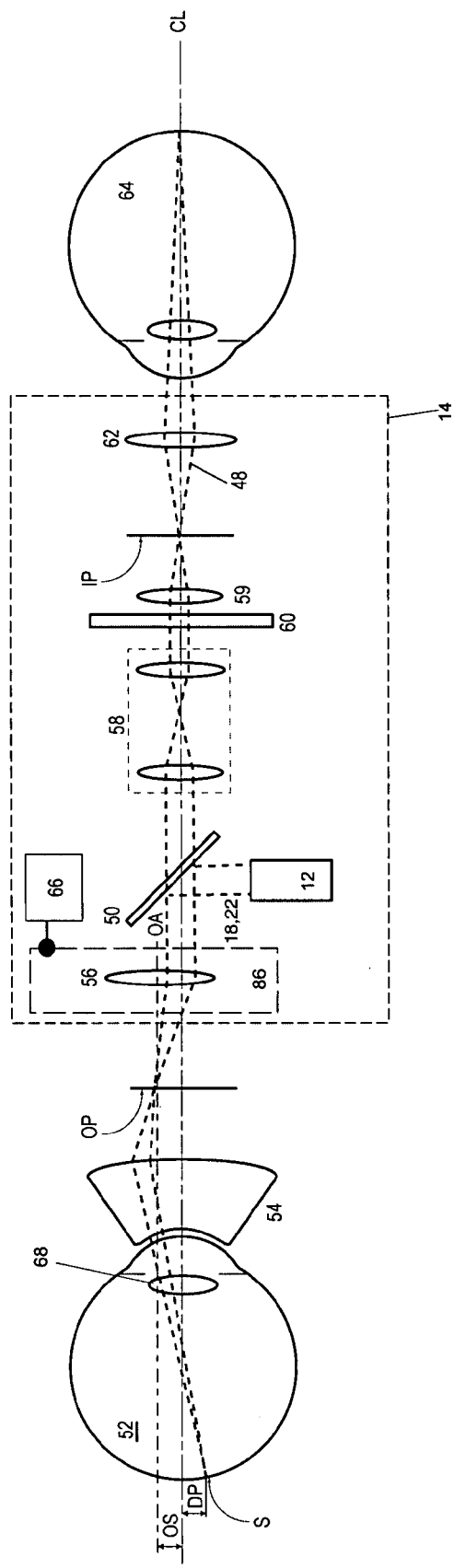
FIG. 11 is a schematic view the ophthalmic surgical device in which a lens is translated to simultaneously move the treatment beam and the physician's field of view.
Figure 12:
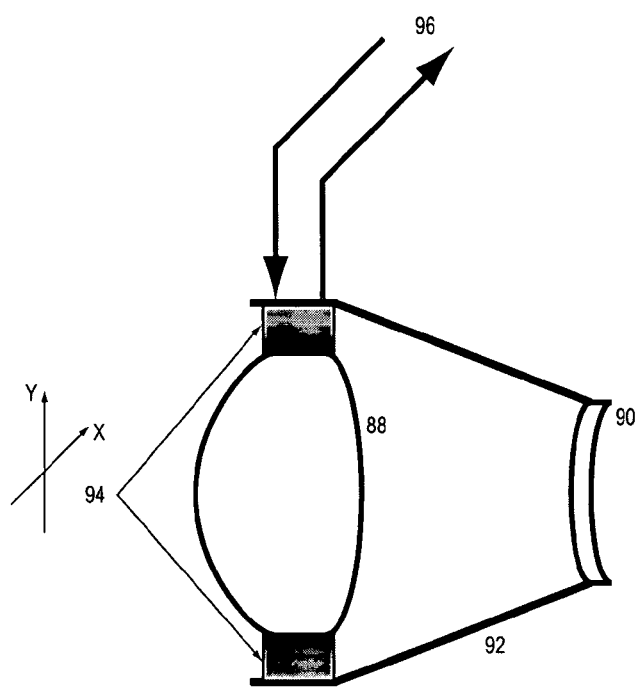
FIG. 12 is a side cross-sectional view of an ophthalmic contact lens with a movable lens that is translated to simultaneously move the treatment beam and the physician's field of view.

FIG. 12 illustrates another embodiment similar to that of FIG. 11. Instead of moving any components in the microscope 14, a lens 88 internal to the ophthalmic lens 54 can be translated. In this configuration, ophthalmic lens 54 includes the lens 88, a contact plate 90 (which contacts the patient's eye), a housing 92, and a translating device 94 (which can include any of the moving devices described above) that moves the lens 88 in the x and y directions. Control lines 96 may be connected to the input/output device 42. Translating the lens 88 via translation device 94 allows for the image of the patient's eye to move in the object plane OP, thus moving spot 76 on the target tissue. Although an ophthalmic lens with a contact plate 90 is shown, it is not required. It is possible to use an ophthalmic lens that does not contact the patient's eye. In the case of a non-contact ophthalmic lens, only housing 92, lens 88, and control lines 96 are included.

Figure 13:
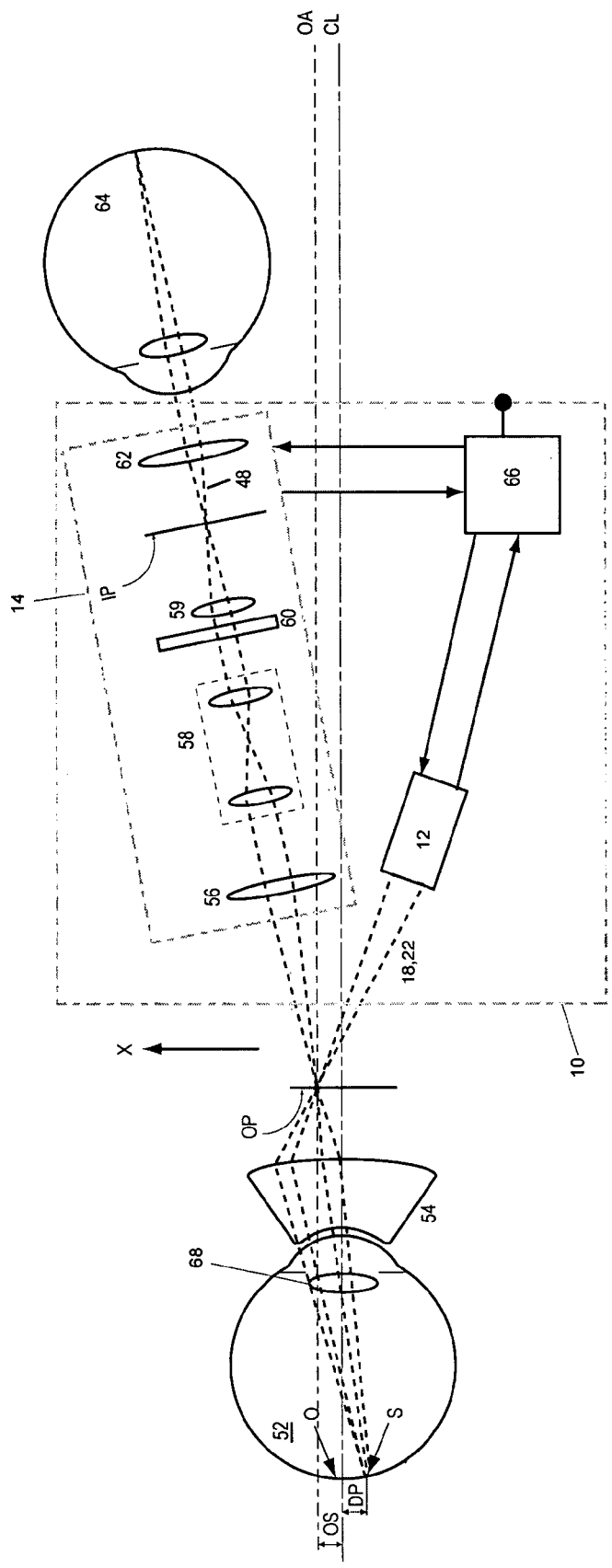
FIG. 13 is a schematic view the ophthalmic surgical device in which the laser system and the microscope are translated to simultaneously move the treatment beam and the physician's field of view, where the treatment beam and visualization beam are spatially separate except for the point at which they cross each other.

FIG. 13 shows an embodiment similar to that of FIG. 1, where beam 18, 22 from the light source assembly 12 and the visualization beam 48 through the microscope 14 are spatially separated and made to point to a common location in object plane OP created by lens 54. Thus, the system includes three optical devices that "look" in different directions, but share a common point S in the patient's eye 52. Such a configuration allows for easy integration with existing devices, as the optical train of the visualization system does not need to be altered to accommodate the light source assembly 12. Furthermore, in the manner described with respect to FIG. 7, a heads-up display type device similar to reticle device 84 may be added at location IP to provide a dynamic display of the beam position in the patient's eye 52 to the physician (by having the movement of translation device 66 controlled and monitored by control electronics 40). In this configuration, the visualization system need not move at all, but still show the physician the ultimate disposition of beams 18, 22.

Figure 14:
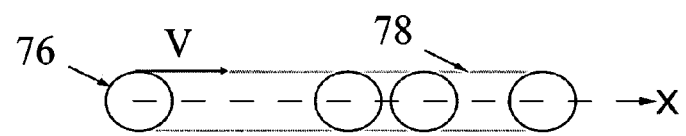
FIG. 14 is a target plane plan view of a pattern of spots of treatment light generated by the ophthalmic surgical device, with irregular spacing between the spots.

It is to be understood that the present invention is not limited to the embodiment(s) described above and illustrated herein, but encompasses any and all variations falling within the scope of the appended claims. For example, the spacing between consecutive spots can be altered as shown in FIG. 14 by varying the magnitude of velocity-V or by pulsing the light source with varying interval times, to result in the irregular spot spacing. While linear scanning is described above, arc or circular beam movement (such as that shown in FIG. 15) can also be implemented. While the embodiments described above include ophthalmic lens 54, this lens could be omitted from any of these embodiments.

What is claimed is:

1. A surgical device for treating a target tissue, comprising:
   a light source configured to generate a treatment beam of light;
   a mirror configured to reflect the treatment beam toward the target tissue and to direct the treatment beam onto the target tissue;
   a plurality of optical elements configured to generate an image of the target tissue from light emanating from the target tissue;
   a translation device configured to translate the mirror and the plurality of optical elements relative to the target tissue to simultaneously move the treatment beam along the target tissue and a field of view of the target tissue defined by the plurality of optical elements,
       wherein the light source is configured to remain stationary while the minor and the plurality of optical elements are translated; and
   control electronics for controlling the translation device to cause the treatment beam to move along the target tissue in a predetermined pattern.

2. The surgical device of claim 1, further comprising:
   an optical fiber for delivering the treatment beam to the mirror.

3. The surgical device of claim 1, wherein at least one of the plurality of optical elements includes target indicia for visually referencing a location of the target tissue at which the treatment beam is incident on the target tissue.

4. The surgical device of claim 1, wherein the plurality of optical elements further comprises:
   a reticle device for visually marking a location in the image of the target tissue at which the treatment beam is incident on the target tissue.

5. The surgical device of claim 4, wherein the reticle device further displays information about at least one of the treatment beam and an operation of the light source.

6. The surgical device of claim 1, wherein the treatment beam directed onto the target tissue is pulsed, and wherein the predetermined pattern comprises a plurality of spaced apart spots.

7. The surgical device of claim 6, wherein the spots are spaced apart by irregular spacing.

8. The surgical device of claim 1, wherein the predetermined pattern comprises one or more curved or straight lines.

9. The surgical device of claim 1, further comprising:
   a second light source for generating an aiming beam of light, wherein the mirror directs the aiming beam onto the target tissue, and wherein the translation device translates at least one of the second light source, the mirror and the plurality of optical elements relative to the target tissue to simultaneously move the aiming beam along the target tissue and the field of view of the target tissue defined by the plurality of optical elements.

10. The surgical device of claim 1, further comprising:
    a graphic user interface for operating the control electronics.

11. A surgical device for treating a target tissue, comprising:
- a light source configured to generate a treatment beam of light;
- a mirror configured to reflect the treatment beam toward the target tissue and to direct the treatment beam onto the target tissue;
- a plurality of optical elements configured to generate an image of the target tissue from light emanating from the target tissue;
- a translation device configured to translate the light source, the minor and the plurality of optical elements relative to the target tissue to simultaneously move the treatment beam along the target tissue and a field of view of the target tissue defined by the plurality of optical elements; and
- control electronics for controlling the translation device to cause the treatment beam to move along the target tissue in a predetermined pattern.

12. The surgical device of claim 11, wherein at least one of the plurality of optical elements includes target indicia for visually referencing a location of the target tissue at which the treatment beam is incident on the target tissue.

13. The surgical device of claim 11, wherein the plurality of optical elements further comprises:
- a reticle device for visually marking a location in the image of the target tissue at which the treatment beam is incident on the target tissue.

14. The surgical device of claim 13, wherein the reticle device further displays information about at least one of the treatment beam and an operation of the light source.

15. The surgical device of claim 11, wherein the treatment beam directed onto the target tissue is pulsed, and wherein the predetermined pattern comprises a plurality of spaced apart spots.

16. The surgical device of claim 15, wherein the spots are spaced apart by irregular spacing.

17. The surgical device of claim 11, wherein the predetermined pattern comprises one or more curved or straight lines.

18. The surgical device of claim 11, further comprising:
- a second light source for generating an aiming beam of light, wherein the mirror directs the aiming beam onto the target tissue, and wherein the translation device translates at least one of the second light source, the mirror and the plurality of optical elements relative to the target tissue to simultaneously move the aiming beam along the target tissue and the field of view of the target tissue defined by the plurality of optical elements.

19. The surgical device of claim 11, further comprising:
- a graphic user interface for operating the control electronics.

20. A surgical device for treating a target tissue, comprising:
- a light source configured to generate a treatment beam of light;
- a mirror configured to reflect the treatment beam toward the target tissue and to direct the treatment beam onto the target tissue;
- a plurality of optical elements configured to generate an image of the target tissue from light emanating from the target tissue;
- a translation device configured to translate the mirror and some but not all of the plurality of optical elements relative to the target tissue to simultaneously move the treatment beam along the target tissue and a field of view of the target tissue defined by the plurality of optical elements; and
- control electronics for controlling the translation device to cause the treatment beam to move along the target tissue in a predetermined pattern.

21. The surgical device of claim 20, wherein at least one of the plurality of optical elements includes target indicia for visually referencing a location of the target tissue at which the treatment beam is incident on the target tissue.

22. The surgical device of claim 20, wherein the plurality of optical elements further comprises:
- a reticle device for visually marking a location in the image of the target tissue at which the treatment beam is incident on the target tissue.

23. The surgical device of claim 22, wherein the reticle device further displays information about at least one of the treatment beam and an operation of the light source.

24. The surgical device of claim 20, wherein the treatment beam directed onto the target tissue is pulsed, and wherein the predetermined pattern comprises a plurality of spaced apart spots.

25. The surgical device of claim 24, wherein the spots are spaced apart by irregular spacing.

26. The surgical device of claim 20, wherein the predetermined pattern comprises one or more curved or straight lines.

27. The surgical device of claim 20, further comprising:
- a second light source for generating an aiming beam of light, wherein the mirror directs the aiming beam onto the target tissue, and wherein the translation device translates at least one of the second light source, the mirror and the plurality of optical elements relative to the target tissue to simultaneously move the aiming beam along the target tissue and the field of view of the target tissue defined by the plurality of optical elements.

28. The surgical device of claim 20, further comprising:
- a graphic user interface for operating the control electronics.

29. A surgical device for treating a target tissue, comprising:
- a light source configured to generate a treatment beam of light;
- a lens configured to direct the treatment beam onto the target tissue;
- a plurality of optical elements configured to generate an image of the target tissue from light emanating from the target tissue, wherein the light emanating from the target tissue passes through the lens and to the plurality of optical elements;
- a translation device configured to translate the lens relative to the target tissue to simultaneously move the treatment beam along the target tissue and a field of view of the target tissue defined by the plurality of optical elements;
- control electronics for controlling the translation device to cause the treatment beam to move along the target tissue in a predetermined pattern;
- a housing; and
- a contact element mounted to the housing for making contact with a patient's eye, wherein the lens is mounted to the housing via the translation device, and wherein the translation device moves the lens relative to the housing.

30. The surgical device of claim 29, wherein at least one of the plurality of optical elements includes target indicia for visually referencing a location of the target tissue at which the treatment beam is incident on the target tissue.

31. The surgical device of claim 29, wherein the plurality of optical elements further comprises:
- a reticle device for visually marking a location in the image of the target tissue at which the treatment beam is incident on the target tissue.

32. The surgical device of claim 31, wherein the reticle device further displays information about at least one of the treatment beam and an operation of the light source.

33. The surgical device of claim 29, wherein the treatment beam directed onto the target tissue is pulsed, and wherein the predetermined pattern comprises a plurality of spaced apart spots.

34. The surgical device of claim 33, wherein the spots are spaced apart by irregular spacing.

35. The surgical device of claim 29, wherein the predetermined pattern comprises one or more curved or straight lines.

36. The surgical device of claim 29, further comprising:
a second light source for generating an aiming beam of light, wherein the lens directs the aiming beam onto the target tissue, and wherein the translation device translates at least one of the second light source, the lens and the plurality of optical elements relative to the target tissue to simultaneously move the aiming beam along the target tissue and the field of view of the target tissue defined by the plurality of optical elements.

37. The surgical device of claim 29, further comprising:
a graphic user interface for operating the control electronics.

38. A surgical device for treating a target tissue, comprising:
a light source configured to generate a treatment beam of light;
an optical element configured to direct the treatment beam onto the target tissue;
a plurality of optical elements configured to generate an image of the target tissue from light emanating from the target tissue;
a translation device configured to translate the light source and the plurality of optical elements relative to the target tissue to simultaneously move the treatment beam along the target tissue and a field of view of the target tissue defined by the plurality of optical elements,
wherein the optical element is configured to remain stationary while the light source and the plurality of optical elements are translated; and
control electronics for controlling the translation device to cause the treatment beam to move along the target tissue in a predetermined pattern.

39. The surgical device of claim 38, wherein:
the treatment beam follows a first optical path from the light source, through the optical element and to the target tissue;
the light emanating from the target tissue follows a second optical path from the target tissue, through the optical element, and through the plurality of optical elements; and
the first and second optical paths are spatially separated but cross each other at a common location.

40. The surgical device of claim 39, wherein:
the plurality of optical elements includes a lens that defines an object plane; and
the common location is located at the object plane.

41. The surgical device of claim 38, wherein at least one of the plurality of optical elements includes target indicia for visually referencing a location of the target tissue at which the treatment beam is incident on the target tissue.

42. The surgical device of claim 38, wherein the plurality of optical elements further comprises:
a reticle device for visually marking a location in the image of the target tissue at which the treatment beam is incident on the target tissue.

43. The surgical device of claim 42, wherein the reticle device further displays information about at least one of the treatment beam and an operation of the light source.

44. The surgical device of claim 38, wherein the treatment beam directed onto the target tissue is pulsed, and wherein the predetermined pattern comprises a plurality of spaced apart spots.

45. The surgical device of claim 44, wherein the spots are spaced apart by irregular spacing.

46. The surgical device of claim 38, wherein the predetermined pattern comprises one or more curved or straight lines.

47. The surgical device of claim 38, further comprising:
a second light source for generating an aiming beam of light, wherein the optical element directs the aiming beam onto the target tissue, and wherein the translation device translates at least one of the second light source, the optical element and the plurality of optical elements relative to the target tissue to simultaneously move the aiming beam along the target tissue and the field of view of the target tissue defined by the plurality of optical elements.

48. The surgical device of claim 38, further comprising:
a graphic user interface for operating the control electronics.

* * * * *